United States Patent [19]

Lundberg

[11] Patent Number: 4,677,846
[45] Date of Patent: Jul. 7, 1987

[54] METHOD OF MEASURING AND REGULATING THE CONCENTRATION OF A FIBRE SUSPENSION AND A DEVICE FOR CARRYING OUT THE METHOD

[75] Inventor: Peter Lundberg, Åmål, Sweden
[73] Assignee: Eur-Control Kalle AB, Sweden
[21] Appl. No.: 829,123
[22] PCT Filed: Apr. 9, 1985
[86] PCT No.: PCT/SE85/00166
§ 371 Date: Nov. 27, 1985
§ 102(e) Date: Nov. 27, 1985
[87] PCT Pub. No.: WO85/04716
PCT Pub. Date: Oct. 24, 1985

[30] Foreign Application Priority Data
Apr. 6, 1984 [SE] Sweden ................................ 8401950

[51] Int. Cl.⁴ .......................................... G01N 11/00
[52] U.S. Cl. ........................................... 73/63; 73/54
[58] Field of Search ........................................ 73/63, 54

[56] References Cited
U.S. PATENT DOCUMENTS
3,286,507 11/1966 Moore .................................. 73/54 X
3,474,663 10/1969 Whitmer et al. ........................ 73/54
4,062,226 12/1977 Hietala ................................. 73/63
4,148,215 4/1979 Hofstetter, Jr. ......................... 73/54

FOREIGN PATENT DOCUMENTS
1233881 6/1971 United Kingdom .................... 73/54
300559 6/1971 U.S.S.R. ............................... 73/63

Primary Examiner—Stewart J. Levy
Assistant Examiner—Joseph W. Roskos
Attorney, Agent, or Firm—Ostrolenk, Faber, Gerb & Soffen

[57] ABSTRACT

The invention relates to a method and device for measuring and regulating the concentration, preferably of a fibre suspension, with the aid of a blade (1) pivotally suspended in the suspension. The blade (1) is caused to pivot such that its trailing end (8) moves between two end positions (A,B) in the suspension for providing a predetermined angular stroke (α). Time measurement is carried out when the trailing edge (8) of the blade (1) moves through its stroke from its upper end position (A) to its lower end position (B). The time obtained is a parabolic function of the concentration and varies in response to the shear force resistance in the fibre suspension of the blade (1) during its angular stroke, and thus in response to the concentration of solid substances in the suspension.

9 Claims, 12 Drawing Figures

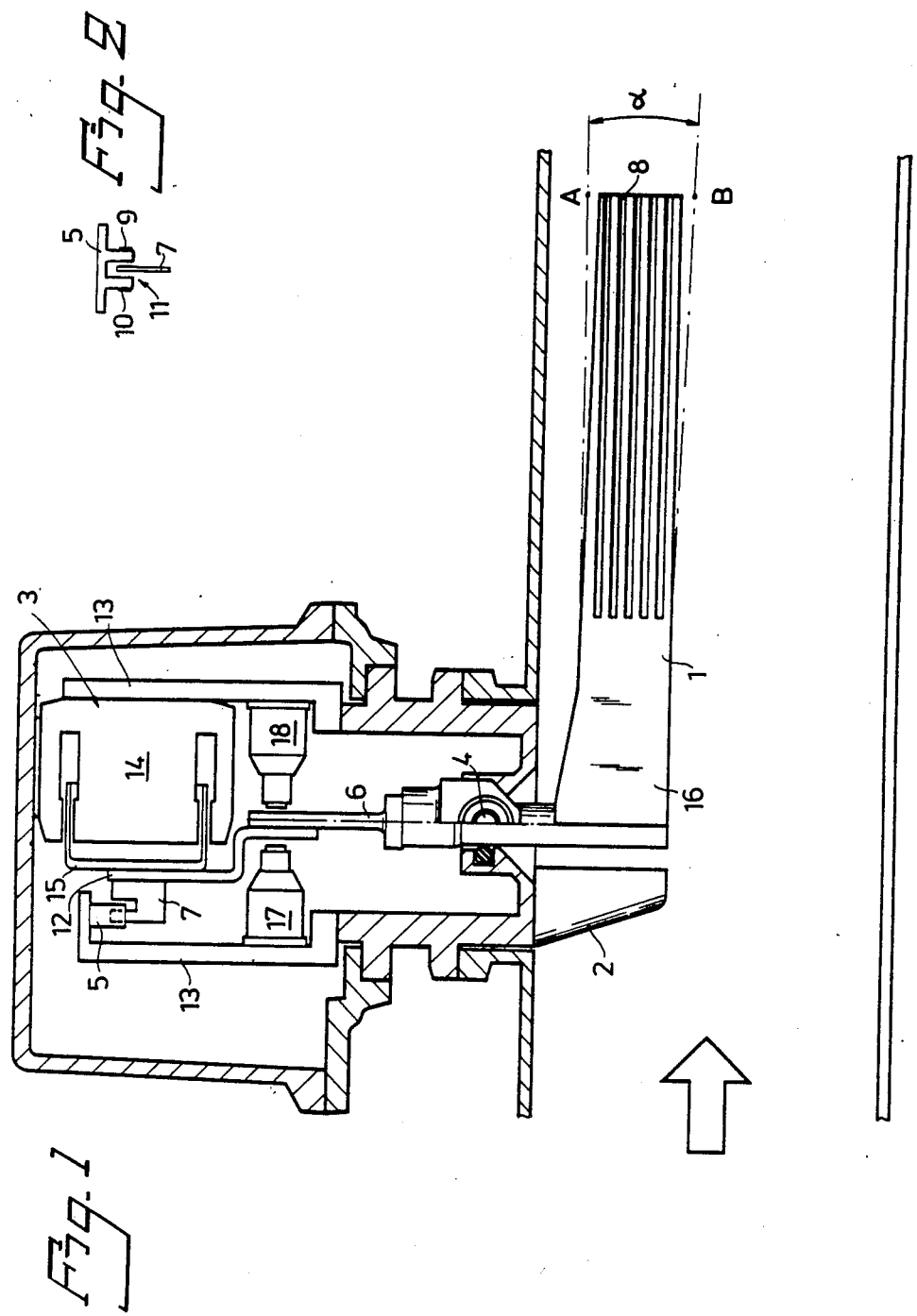

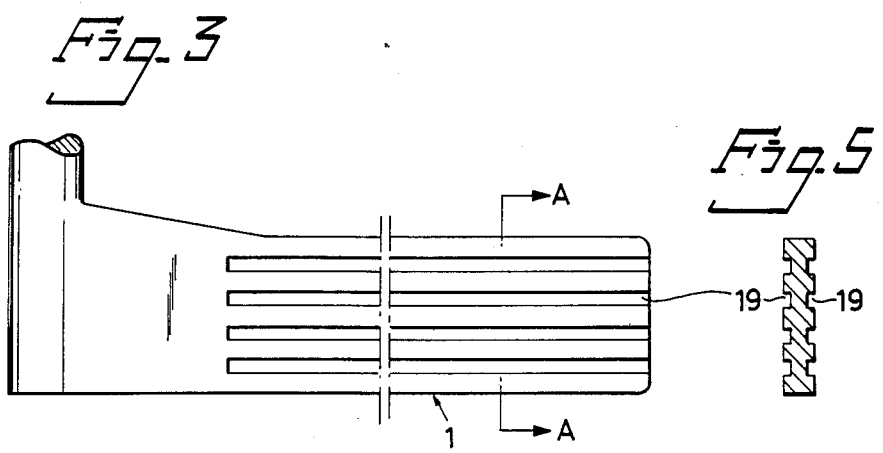
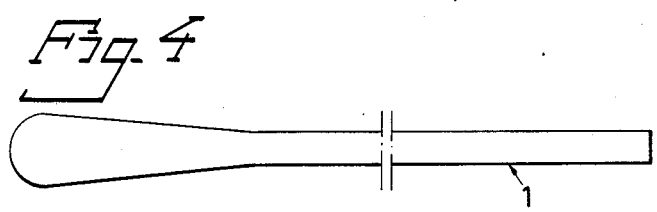
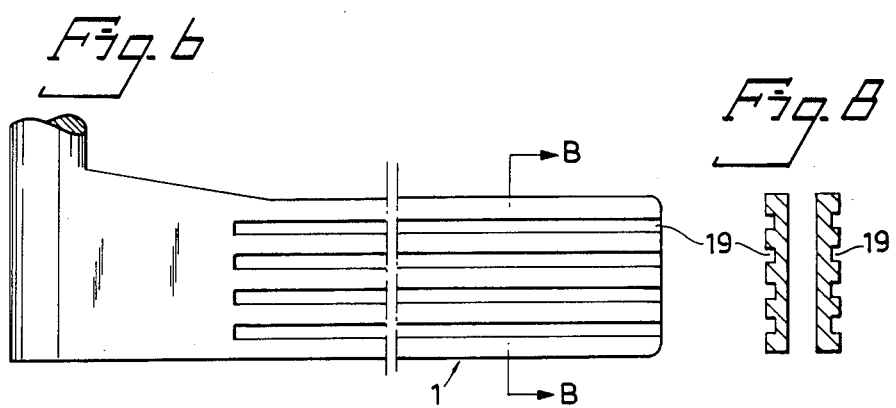
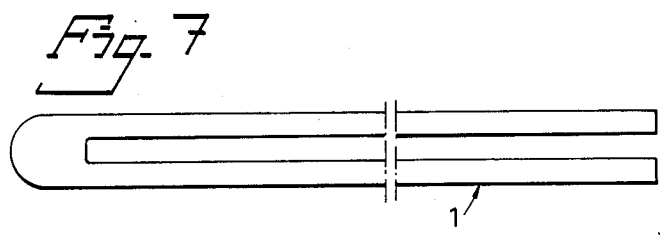

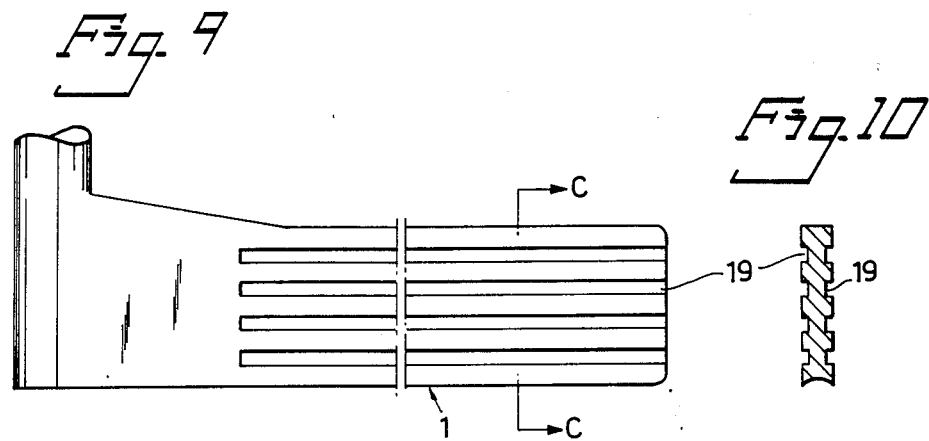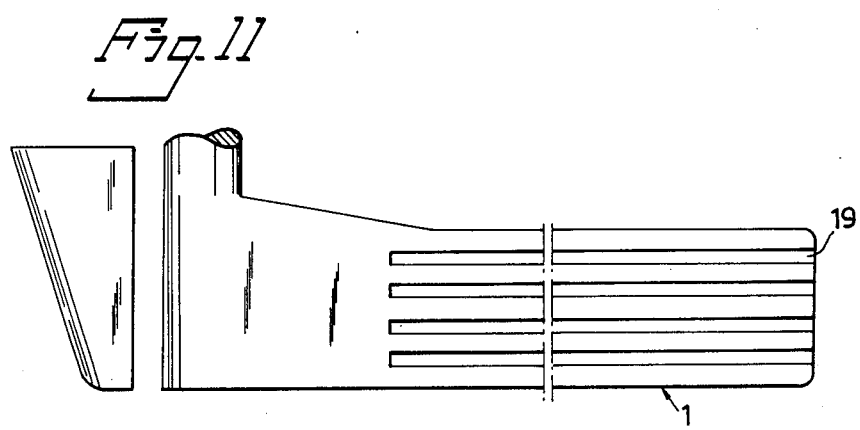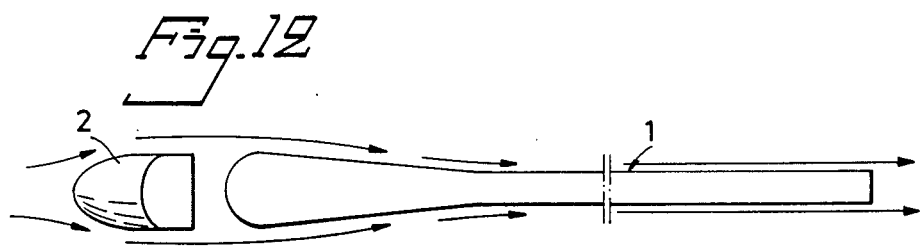

METHOD OF MEASURING AND REGULATING THE CONCENTRATION OF A FIBRE SUSPENSION AND A DEVICE FOR CARRYING OUT THE METHOD

The present invention relates to measuring and regulating the concentration of a fibre suspension, particularly within the pulp and paper industry, although the invention may be used within other areas, such as measuring the dry substance content in sewage sludge, peat suspensions, mineral wool suspensions etc.

Three main groups of transducers may be recognised for measuring the concentration of fibre suspensions, namely shear force transducers, optical transducers and transducers working with pressure drop changes or flow speed changes depending on pulp concentration. There are further groups of subordinate importance. Transducers working according to the shear force principle may be divided into two main groups, namely rotating and static transducers.

The transducer of the present invention may be suitably placed in the group "static transducers", although there are certain principle differences compared with other devices in the group. Colloquially, these transducers are called static or stationary transducers, shark fins, blade transducers and fins. The static transducers compete to a minor extent with the rotating type, since the latter usually have better measuring accuracy, higher sensitivity, less flow sensitivity shorter unactivated times etc. Users install static transducers primarily in positions where performance requirements are not too high.

The static transducers known up to now include a pivotably suspended blade placed in the pulp flow. The suspension most usually comprises some form of mounting and a seal against the medium. Due to the flow speed in the conduit there is a shear force moment on the blade, this moment being converted to a standardized output signal, which may be pneumatic or electric. The moment converters work either according to the weighing balance principle or the force balancing principle. It is thus the front edge of the blade exposed to the flow which cuts through the fibre flow to generate the shear force moment. Since the working principle requires that the medium is in movement, it is easy to understand that a certain, undesired flow sensitivity occurs. The manufacturers have attempted to solve this problem by resorting to more or less sophisticated implementations of the blade. The results of these efforts vary, but the general opinion is that the dependency on flow in static transducers is one of three dominating problem areas for the group as a whole. The consequence has thus been that the manufacturers stipulate relatively tight flow ranges within which the transducers may be used, around 0.5–3 m/s and in some cases as tight as 0.3–1.5 m/s. To obtain a flow within these limits the conduit must be tapered diverging or converging in certain cases, which considerably increases the installation. The next problem area is also brought about by the measuring principle, since the blades are usually relatively voluminous and occupy 80–95% of a 100 mm diameter conduit. The formation of plugs or the presence of larger solid bodies moving with the fibre flow in the conduit quite often damages the blade and its suspension. The front edge of the blade cannot, of cource, be protected by a barrier placed too close it, since the measuring result would then be compromised. A smaller barrier protecting the suspension shaft of the blade is usually integrated in the structure, however. Effective damping systems cause some makes to be less sensitive to vibrations than others.

It was mentioned in the introduction that rotating transducers give greater sensitivity to concentration changes. This is a generally accepted fact, and the chief reason for there being little competitionbetween the groups. The higher relative difference in speed between sensor and fibre network in rotating transducers gives a higher moment level, in spite of the minor size of the sensor, and in turn this results in higher sensitivity and better signal/noise relationship. This becomes particularly noticeable for low concentrations. While static transducers may be used down to 1.5–1.75% concentration, the rotating type often measure down in the concentration range of 0.8–1%. To do justice to a comparison between rotating and static transducers, it should also be mentioned that the price of a static transducer is 3–4 times lower than that of the rotating type.

The object of the present invention is to provide a new method and a new device for measurement of the kind mentioned in the introduction, where the limitations and disadvantages of conventional static transducers have been eliminated. This object is achieved by the method and device in accordance with the invention having been given the characterizing features disclosed in the following claims.

By means of the present invention there is provided a method and device for measuring and regulating the concentration of a fibre suspension where, in comparison with other already known stationary transducers, the following advantages should be mentioned: the blade only blanks off a minor part of the conduit diameter and is entirely protected by a barrier arranged in front of it, flow dependency is less because of the fully covering barrier, the relative movement of the blade itself with respect to the fibre network results in that the flow speed range can be increased downwards, in certain concentration ranges the flow range will be 0.15–5 m/s (for a blade length of 0.15 m), the active blade gives greater sensitivity for concentration changes within the concentration range of 1.5–3% and that vibration sensitivity is low, since the blade is only active for a very short time, 0.04–2.0% of the total time, and is locked by magnetic force in its rest position, and finally that the number of moving parts is less than in other transducers.

The invention will now be described in detail with reference to the accompanying drawing, on which FIG. 1 illustrates, partly in section, a device in accordance with the present invention installed in a conduit, FIG. 2 is a schematic side view of the optical reading fork, illustrated in FIG. 1, FIG. 3 is a side view of a blade, FIG. 4 is a view from below of the blade illustrated in FIG. 3, FIG. 5 is a section along the line A—A through the blade illustrated in FIG. 3, FIG. 6 is a side view of an alternative embodiment of the inventive blade, FIG. 7 is a view from below of the blade illustrated in FIG. 6, FIG. 8 is a section along the line B—B through the blade illustrated in FIG. 6, FIG. 9 is a side view of an alternative embodiment of the inventive blade, FIG. 10 is a section along the line C—C through the blade illustrated in FIG. 9, FIG. 11 is a side view of an alternative embodiment of the inventive blade, and FIG. 12 is a view from below of the blade illustrated in FIG. 11.

A transducer device in accordance with the present invention is illustrated partially sectioned in FIG. 1, where it is shown with its blade pivotally mounted in a conduit, through which flows the medium that is measured. The blade 1 is smaller than is general in static transducers and only occupies 30–40% of the conduit diameter, where the diameter of the conduit is 100 mm. The whole of the front end 16 of the blade 1 is protected by a streamlined barrier 2, which is situated in front of the blade 1, seen in the flow direction. A system of forces in the form of an electromagnetic system 3 is arranged to activate the blade 1 via a suspension shaft 6, so that the blade 1 can pivot about a bearing 4. The free or trailing edge 8 of the blade 1 moves a distance A-B during a given time. The time for the blade 1 to execute this angular stroke α is a parabolic function of the concentration of the medium. The inventive transducer device works, as will be seen, according to the shear force principle, but the blade 1 has a movement of its own, and is not dependent on the flow in the conduit for the occurrence of shear forces. After termination of the angular stroke A-B, the current to the electro-magnetic system 3 is pole-reversed, and the trailing edge 8 of the blade 1 moves through the distance B-A, i.e., it returns to its initial position.

The blade 1 moves at a rate ranging from one stroke per second (1.0 Hz) to one stroke every five seconds (0.2 Hz).

An electronic amplifier unit, not illustrated on the drawing, measures the time for the stroke A-B with the aid of an optical reading fork 5 including an IR-light-emitting diode 9 (LED) and a detector 10, the gap 11 of which is traversed by a beam interrupter 7 attached to the suspension shaft 6. The amplifier evaluation unit sums five timeperiods, for example, and gives a mean value thereof to form a representative time for the five executed strokes. For each new stroke the first time of the five is subtracted and the new time is added, which gives a continuous mean value formation of the time for one stroke. The system 3 is situated at the free end 12 of the suspension shaft 6, and comprises a solenoid magnet 14 fixed to the device housing 13 for co-action with a plunger coil 15 arranged at the free end 12 of the suspension shaft 6, such as to provide the pivoting or swinging movement of the blade 1 about the bearing 4. The optical fork 5 is also fixed to the casing 13 in the region of the free end 12 of the suspension shaft 6. The bearing 4 carrying the blade 1 is situated on the suspension shaft 6, close to the forward end 16 of the blade. Between the bearing 4 and the free end 12 of the shaft 6 there are mechanical - stroke limiting means 17, 18 for arresting the swinging movement of the suspension shaft 6.

The mentioned mean time value is presented by the amplifier unit as a standard output signal, e.g., 0–20 mA or 4–20 mA.

In reality, the time measurement is made during a portion of the stroke, the beam interrupter 7 interrupting the light beam between the legs of the optical fork 5. The beam interrupter 7 has a width corresponding to 50–80% of the total stroke. The reason for this is to prevent a false signal, should there be bounce when the magnetic system reaches its end positions, if the beam interrupter 7 corresponds to or lies too close to, the total stroke. The system 3 is about 100 mm away from the bearing 4, and has a total stroke of about 4 mm. Consequently, the distance A-B moved through by the trailing edge 8 of the blade 1 is about 8 mm if the distance to the bearing 4 is about 200 mm. The measurement time will, of course, vary heavily with the configuration of the blade 1, type of medium that is measured, beam interrupter etc. Typical measurement times are 2–20 m/s.

As will be seen from FIGS. 3–12, the blade 1 can be implemented in several different ways to suit different types of medium which is to be measured. The basic type of blade for long-fibre suspensions with a high network strength is a single blade with longitudinal grooves 19 on both sides, see FIGS. 3–5. The grooves 19 increase the total area of the blade and reduce its weight. Furthermore, the number of edges and sides which are to cut through the fibre network increase with the number of grooves. This gives a comparatively high shear force level.

Short-fibre suspensions with low network strength sometimes require other configurations, e.g., a double blade with longitudinal grooves 19 on the outsides of the blades 1, see FIGS. 6–8. For extremely low network strengths, both the single blade and the double blade may be provided with concave bottom surfaces 20 in the measuring direction, see FIGS. 9–10. This provides a certain dewatering of the suspension in front of the blade 1 in the measuring direction and contributes to increasing the shear force level. Common to all the embodiments of the blade 1 is that its shape conforms well to the shape of the barrier 2, so that together they form a profile which gives the least possible disturbance to the flow picture, see FIGS. 11–12. This contributes to small dependence on the flow. It has been stated hereinbefore that the transducer according to the present invention is not dependent on the flow of the medium to be measured for shear forces to occur. However, there is a least flow which may be accepted. This minimum flow is 0.15 m/s if the blade 1 is activated once per second for a blade length of 0.15 m, 0.4 m/s if the blade 1 is activated twice per second and so on. Since more rapid activation that once per second is not necessary, 0.15 m/s is a suitable minimum flow rate. It is thus guaranteed that the blade always cuts through a representative sample of the medium to be measured. If the blade 1 is activated more rapidly simultaneously as the flow rate is low, the result could be that fibre flocks in the suspension are thrust away and replaced by pure liquid, which lowers the output signal.

What is claimed is:

1. A method of measuring and regulating the concentration of a fibre suspension, with aid of a blade (1) pivotally suspended in the suspension, said blade being caused to pivot such that its free of trailing edge (8) moves between two end positions (A-B) in the suspension to provide a predetermined angular stroke (α), wherein the blade (1) pivots intermittently and with a constant force, at least in the measuring direction in the suspension, between both end positions (A and B) with a stroke exceeding 1 mm at the trailing edge (8) of the blade (1), time measurement being carried out when the trailing edge (8) moves through a 50–80% portion of the angular stroke (α), said portion being situated at an equal distance from the upper end position (A) and lower end position (B) of the stroke (α), said time having a value which is a parabolic function of the concentration and varying in response to the shear force resistance in the fibre suspension of the blade (1) during its angular stroke, and thus in response to the concentration of solid substances in the suspension.

2. A method as claimed in claim 1, wherein the blade (1) is caused to pivot with the aid of an electro-magnetic system (3) via a suspension shaft (6) with a frequency lying between 1.0–0.2 Hz.

3. A method as claimed in claim 1 or 2, wherein the trailing edge (8) of the blade (1) is given a greatest amplitude in the order of magnitude (8 mm) for a distance to the bearing (4) carrying the blade (1) of about 200 mm.

4. A method as claimed in claim 1, wherein the blade (1) is caused to pivot in a plane in the fibre suspension, substantially coinciding with the chief plane of the blade (1).

5. A device for measuring the regulating concentration of a fibre suspension, comprising a blade (1) pivotally suspended in the suspension, means (3) for causing the blade (1) to pivot with the aid of a suspension shaft (6) about a bearing (4) pivotally suspending the blade, and also a time measurement means, wherein the means for causing the blade (1) to pivot comprises an electromagnetic system (3) situated at the free end (12) of the suspension shaft (6) and arranged to pivot the blade (1) such that its free or trailing edge (8) moves with a frequency of 1.0–0.2 Hz between two end positions (A-B) in the fibre suspension to achieve an angular stroke ($\alpha$) of a predetermined distance, and wherein the time measurement means comprises an electronic amplifier unit which acts with the aid of an optical reading fork (5) fixed in the casing (13) of the measuring device, the fork including an IR light emitting diode (9) and detector (10), the gap (11) of the fork (5) accommodating a beam interrupter (7), attached to the free end (12) of the suspension shaft (6) and arranged to interrupt the light from the light emitting diode (9) when the end (12) pivots, to measure the time during a Predetermined portion of the angular stroke ($\alpha$) at the movement of the blade (1) from its upper end position (A) to its lower end Position (B), said time having a value corresponding to a parabolic function of the concentration and varying in response to the shear force resistance of the blade (10) in the fibre suspension during its angular stroke ($\alpha$) and thus in response to the concentration of solid substances in the suspension.

6. A device as claimed in claim 5, wherein the electromagnetic system (3) comprises a solenoid magnet (14) fixed in the casing (13) of the measuring device, for co-action with a plunger coil (15) arranged on the free end (12) of the suspension shaft (6) for Providing the pivoting movement of the blade (1) about the bearing (4).

7. A device as claimed in claim 5, wherein the bearing (4) carrying the blade (1) and shaft (6) is situated close to the forward end (16) of the blade (1) for coaction with the shaft (6), and a barrier (2) is situated upstream of the forward end (16) of the blade (1) to protect the blade and contribute to low dependence on the flow of the medium to be measured.

8. A device as claimed in claim 5, wherein the blade (1) has the form of an elongate plate with longitudinal grooves (19) on both sides, said plate being formed with a concave bottom (20) at its lower edge, seen in the measuring direction, for increasing the shear force level.

9. A device as claimed in claim 8, wherein the blade (1) is parted in its chief plane, to form a bifurcate blade having longitudinal grooves (19) along its two outer faces.

* * * * *